United States Patent [19]

Molina

[11] Patent Number: 5,780,011
[45] Date of Patent: Jul. 14, 1998

[54] PROCESS OF MAKING RADIOLOGICAL CONTRAST FOR GASTROINTESTINAL EXPLORATION COMPRISING BARIUM SULFATE AND SUCRALFATE

[75] Inventor: Ramon Gallo Molina, Madrid, Spain

[73] Assignees: Industrial Farmaceutica Cantabria S.A.; Gallo De Llanos S.L., both of Madrid, Spain

[21] Appl. No.: 691,078

[22] Filed: Aug. 1, 1996

[30] Foreign Application Priority Data

Aug. 2, 1995 [ES] Spain ................................. 9501574

[51] Int. Cl.⁶ ....................................... A61K 49/04
[52] U.S. Cl. ............................... 424/9.41; 424/9.411
[58] Field of Search .................... 424/9.41, 9.411

[56] References Cited

U.S. PATENT DOCUMENTS

| | | | |
|---|---|---|---|
| 5,023,072 | 6/1991 | Cheng | 424/9 |
| 5,370,901 | 12/1994 | Tournier et al. | 427/2.12 |
| 5,518,730 | 5/1996 | Fuisz | 424/426 |
| 5,580,579 | 12/1996 | Ruddy et al. | 424/489 |
| 5,628,981 | 5/1997 | Liversidge et al. | 424/9.4 |

FOREIGN PATENT DOCUMENTS 0526862   2/1993   European Pat. Off.

*Primary Examiner*—Gary E. Hollinden
*Attorney, Agent, or Firm*—Wolf, Greenfield & Sacks, P.C.

[57] ABSTRACT

A procedure for obtaining extemporaneous and direct use radiological contrast formulations for gastrointestinal exploration, comprising a radio-opaque contrast based on a micronized barium sulfate and a substance, i.e. sucralfate, which permits the selective adherence of the contrast to the injured zone and is obtained by interposing the barium sulfate in the sucralfate paste in an acid medium.

These formulations are appropriate for being administered orally or rectally.

9 Claims, No Drawings

PROCESS OF MAKING RADIOLOGICAL CONTRAST FOR GASTROINTESTINAL EXPLORATION COMPRISING BARIUM SULFATE AND SUCRALFATE

The present invention relates to a procedure for obtaining a new galenic radio-opaque formulation which reinforces the image, increases contrast sharpness and, by specifically adhering to the injury, allows for subsequent verification.

A procedure is described whereby radio-opaque preparations are obtained for gastroenteritic radiological diagnosis. Said formula contains, in addition to the micronized radio-opaque barium sulfate, a sucrose and aluminum by-product, i.e. sucralfate.

The formulations thus obtained are appropriate for radio-diagnosis, and provide substantial advantages over current formulations. Namely, they are easy to use;

allow a lower radio-opaque concentration to be applied;

enhance the radiological image signal;

increase contrast;

provide greater image sharpness; and allow the injury to be confirmed once the contrast has been drained from the gastroenteritis cavity.

BACKGROUND AND STATE OF THE ART

A review of the current radio-opaque preparation systems used in gastroenteritic radio-diagnosis indicates that they offer improvements only in regard to the organoleptic features of the various preparations. This invention provides a difference in that the barium salt is bound to the ulcered mucous membrane for a period of time and in a specific manner as a result of the sucralfate's binding capability to the ulcer's proteins.

The new procedure proposed herein permits formulations to be obtained comprising a radiographic contrast, a micronized barium sulfate and a substance enabling selective adherence to gastroenteric injuries, thereby providing a clearer radiological image of an enhanced sharpness for a longer period of time.

GENERAL DESCRIPTION

The procedure for obtaining these preparations involves suspending the barium sulfate in the paste formed by the sucralfate in an acid medium.

The formulas and procedures for this purpose, according to the invention, are illustrated hereunder by the following examples which must not be interpreted as restrictive of the scope of the invention.

Formulations may be prepared for extemporaneous and for immediate use (suspension), administered both orally and rectally.

EXAMPLE A

Preparation for extemporaneous use, administered orally

1) Suspend the sucralfate in water.
2) Knead the barium sulfate into the paste previously obtained.
3) Incorporate the carriers by kneading.

Form granules and dry in warm environment.

| Granulate per 100 g: | |
| --- | --- |
| Micronized barium sulfate | 95 g |
| Sucralfate | 0.9 g |
| Carriers; thickeners, sweeteners and aromatizers, q.s.p | 100 g |

EXAMPLE B

Preparation for immediate use, administered orally

1) Suspend the sucralfate in water.
2) Add hydrochloric acid at pH=3±0.2
3) Knead the barium sulfate into the paste previously obtained.
4) Suspend this mixture in the thickener, sweetener, aromatizer and preserver solution.

Suspension per 100 ml:

| Micronized barium sulfate | 70 g |
| --- | --- |
| Sucralfate | 0.7 g |
| Carriers; thickeners, sweeteners, preservers and aromatizers, q.s.p. | 100 ml |

EXAMPLE C

Preparation for immediate use, administered rectally

1) Suspend the sucralfate in water.
2) Add hydrochloric acid at pH=2.5±0.2
3) Knead the barium sulfate into the paste previously obtained.
4) Suspend this mixture in the thickener, sweetener, aromatizer and preserver solution.

Suspension per 100 ml:

| Micronized barium sulfate | 50 g |
| --- | --- |
| Sucralfate | 0.6 g |
| Carriers; thickeners, sweeteners, preservers and aromatizers, q.s.p. | 100 ml |

Tests

Testing was conducted using formulas similar to the ones described in Examples A and B, according to the following technique.

To 15 ml of preparation, add 4 ml of artificial gastric juice and then heat to 35°. Under these conditions, incorporate animal tissue in order to study the binding properties on the injured tissue. Radiographic tests confirm the advantages over the tests performed using formulations which carry only micronized barium sulfate.

I claim:

1. A process for making a radio-opaque formulation comprising mixing a radiological contrast agent with a gastroenteric injury selective adherence agent in an acid medium.

2. The process of claim 1, wherein the radiological contrast agent is barium sulfate.

3. The process of claim 1, wherein the gastroenteric injury selective adherence agent is sucralfate.

4. The process of claim 1, wherein the acid medium has a pH less than about 3.

5. The process of claim 4, wherein the pH is about 2.5.

6. The process of claim 4, wherein the pH is about 3.

7. The process of claim 1, wherein the radio-opaque formulation is formulated for oral administration.

8. The process of claim 1, wherein the radio-opaque formulation is formulated for rectal administration.

9. The process of claim 1, wherein the radio-opaque formulation is formulated to adhere for a sufficient time to permit radiographic test confirmation after draining the radio-opaque formulation from a gastroenteric cavity.

* * * * *